United States Patent [19]

Mendes et al.

[11] Patent Number: 5,824,099
[45] Date of Patent: Oct. 20, 1998

[54] SURGICAL METHOD AND TOOL FOR REPAIRING A PATELLA OF THE KNEE JOINT

[76] Inventors: David Mendes; Ruth Beer, both of 8 Keller St., Hafia, Israel, 34483

[21] Appl. No.: 735,927

[22] Filed: Oct. 24, 1996

Related U.S. Application Data

[63] Continuation-in-part of Ser. No. 375,085, Jan. 19, 1995, Pat. No. 5,580,353.

[51] Int. Cl.$^6$ ........................................................ A61F 2/38
[52] U.S. Cl. ................................................. 623/20; 606/80
[58] Field of Search .......................... 606/80, 81; 623/20; 128/898

[56] References Cited

U.S. PATENT DOCUMENTS

| | | | |
|---|---|---|---|
| 3,667,456 | 6/1972 | Charnley | 606/81 |
| 4,004,581 | 1/1977 | Heimke et al. | 606/81 |
| 4,273,117 | 6/1981 | Neuhauser | 606/81 |
| 4,284,080 | 8/1981 | Rehder | 606/80 |
| 4,546,501 | 10/1985 | Gustilo et al. | 623/23 |
| 4,944,756 | 7/1990 | Kenna | 623/20 |
| 5,019,104 | 5/1991 | Whiteside et al. | 623/20 |
| 5,246,460 | 9/1993 | Goodfellow et al. | 623/20 |
| 5,295,992 | 3/1994 | Cameron | 606/80 |
| 5,514,141 | 5/1996 | Prizzi Jr. | 606/80 |

*Primary Examiner*—David Isabella
*Attorney, Agent, or Firm*—Mark M. Friedman

[57] ABSTRACT

A surgical method and tool for repairing a natural patella are provided. The method comprises the steps of: (a) preparing a natural patella by removing a portion thereof so as to leave a substantially convex remaining portion; and (b) fixing a patella implant onto the substantially convex remaining portion of the natural patella, the patella implant including: an upper surface for sliding over the femoral articulating member; a substantially concave under surface for fixation to the convex remaining portion of the natural patella; and a circumferential facet.

A surgical tool according to the present invention comprises a substantially concave rotatable reaming member, the concavity of the reaming member being substantially equal to the concavity of the undersurface of the patella implant. The reaming member features a bit for drilling a hole in the natural patella so as to accept a peg connected to the patella implant. Alternatively, the bit may be used for guiding the reaming member through a central pre-drilled hole in the natural patella.

11 Claims, 3 Drawing Sheets

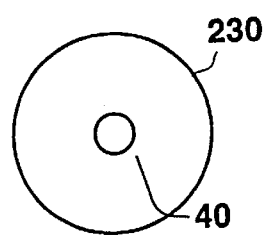
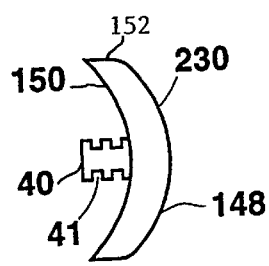
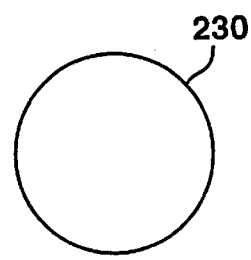
FIG. 4    FIG. 3    FIG. 5
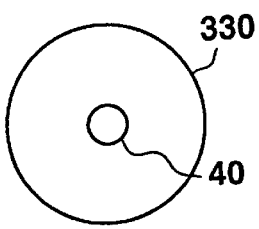
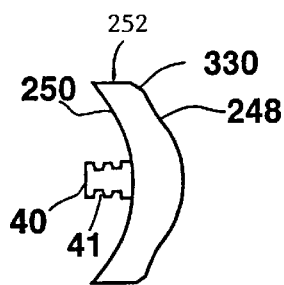
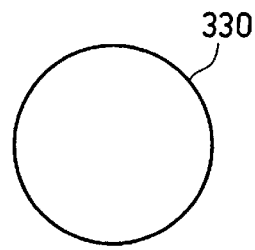
FIG. 7    FIG. 6    FIG. 8
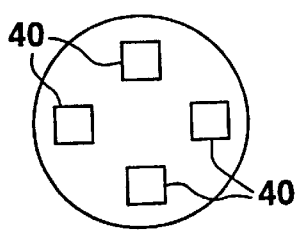
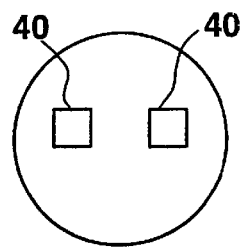
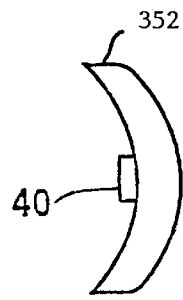
FIG. 10    FIG. 9    FIG. 11
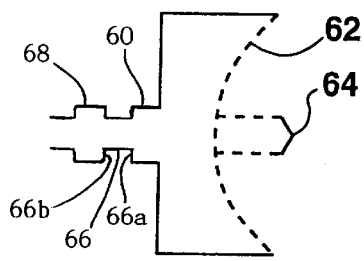
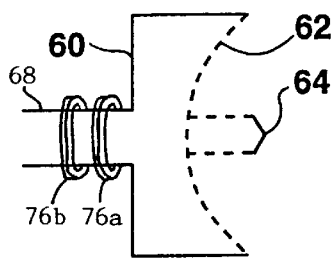
FIG. 12    FIG. 13

5,824,099

SURGICAL METHOD AND TOOL FOR REPAIRING A PATELLA OF THE KNEE JOINT

This is a continuation in part of U.S. patent application Ser. No. 08/375,085, filed Jan. 19, 1995

FIELD AND BACKGROUND OF THE INVENTION

The present invention relates to a surgical method and tool for repairing a natural patella of the knee joint and, more particularly, to a surgical method and tool for reshaping a natural patella and fixing a patella implant to the remaining portion of a natural patella.

Joint replacement is becoming increasingly widespread. One of the most widely practiced joint replacement involves the knee joint. In many cases, the replacement of the knee joint with a prosthesis also involves the replacement of a portion of the patella with a prosthetic.

Partial replacement of the patella is widely used in the surgical replacement of a damaged portion of the knee joint. However, it is known that, in a significant percentage of the cases, the patella implant typically fails after five to fifteen years. One of the typically occurring failures is near or at the periphery of the circular or elliptical patella implant, where the thickness of the patella implant material, typically high molecular weight high density polyethylene (HDPE), is at its smallest. A failing patella could lead to significant pain in the patient and typically requires a second operation to replace the failed patella implant and often the entire prosthetic joint.

U.S. patent application Ser. No. 08/375,085 discloses a prosthetic patella implant adapted to structurally fit a remaining portion of the natural patella with maximal preserving of healthy natural tissue and minimal wear of the implant.

The present invention relates to a surgical method and tool for preparing a natural patella by removing a portion thereof to accept the patella implant described in U.S. patent application Ser. No. 08/375,085.

SUMMARY OF THE INVENTION

According to the present invention there is provided a method of repairing a natural patella, comprising the steps of: (a) preparing the natural patella by removing a portion thereof so as to leave a substantially convex remaining portion; and (b) fixing a patella implant onto the convex remaining portion of the natural patella, the patella implant including: an upper surface for sliding over the femoral articulating member; a substantially concave undersurface for fixation to the substantially convex remaining portion of the natural patella; and a circumferential facet.

According to further features in preferred embodiments of the invention described below, a method according to the present invention further includes the step of drilling at least one hole within the remaining portion of the natural patella for accepting at least one peg, the at least one peg being connected to the patella implant.

The diameter of the patella implant may be substantially equal to the diameter of the natural patella. Alternatively, the diameter of the patella implant may be substantially smaller than the diameter of the natural patella.

The circumferential facet of the patella implant may be cylindrical or conical in shape. A conical circumferential facet may be used for facilitating the attachment of the patella implant to the remaining portion of the natural patella by means of press fitting or other fixation techniques.

According to still further features of the invention described below, the surgical method is carried out using a reamer which includes a concave rotatable reaming member, and preferably one central bit.

Thus, according to the present invention there is further provided a reamer for use in preparing a natural patella to accept a patella implant having a substantially concave undersurface, comprising: a concave rotatable reaming member, the concavity of the reaming member being substantially equal to the concavity of the undersurface.

A reamer according to the present invention may further comprise a central bit protruding from the concave rotatable reaming member for drilling a hole in the natural patella and for guiding the reaming member to a predetermined portion of the natural patella.

Alternatively, a reamer according to the present invention may include a central bit having blunt end for guiding the reaming member through a pre-drilled hole in the natural patella.

The diameter of the reaming member may be substantially equal to or smaller than the diameter of the natural patella.

According to the present invention there is provided a design which will enable the manufacture of a HDPE patella implant with an overall thickness of not less than about 8 mm. This thickness is considered in the scientific literature as an optimal thickness for a high molecular weight high density polyethylene (HDPE) patella implant for use in an average person weighing 60–70 kg or more, for preventing high stresses within the material. Smaller thicknesses are to be used in smaller patients.

The use of the augmented minimum thickness eliminates one of the main causes of failure of patella implants and enhances the durability of the implant.

To provide the required optimal thickness of the patella implant, the natural patella is cut, reamed and trimmed in such a manner as to remove a total of up to about 8 mm or more from the natural bone and cartilage to leave a convex shape which complements the concave shape of the undersurface of the patella implant.

The concave undersurface of the patella implant fits the appropriately reamed remaining portion of the natural patella. The upper surface articulates with the articulating femoral member, typically a groove, and is shaped to fit the corresponding articulating portion of the femoral component of the total knee implant. When the articulating femoral member is a groove, the upper surface of the implant is typically substantially convex. Where the upper surface is convex the convexity of the upper surface and the concavity of the undersurface of a patella implant according to the present invention do not necessarily conform to each other and may be independently varied to accommodate the specific design of the femoral groove and the femoral condyles, or their equivalent, and the convexity of the prepared natural patella.

The present invention successfully addresses the shortcomings of the presently known configurations by providing a surgical method and tool for repairing a natural patella by reshaping the natural patella and fixing a patella implant to the remaining portion of the natural patella, such that the overall combination of patella implant and remaining natural patella features a maximal biomechanical stability. This is achieved by maximizing the volume of the remaining natural patella, minimizing the potential damage to necessary blood vessels at the periphery of the natural patella, conferring an optimal mechanical stability to the implant itself by limiting its minimal thickness to 8 mm or alternatively 6 mm, and providing complementary shapes to the implant and the remaining natural tissue.

BRIEF DESCRIPTION OF THE DRAWINGS

The invention is herein described, by way of example only, with reference to the accompanying drawings, wherein:

FIG. 3 is a cross sectional view of one embodiment of a patella implant according to the present invention;

FIG. 4 is a back view of the patella implant of FIG. 3;

FIG. 5 is a front view of the patella implant of FIG. 3;

FIG. 6 is a cross sectional view of another embodiment of a patella implant according to the present invention;

FIG. 7 is a back view of the patella implant of FIG. 6;

FIG. 8 is a front view of the patella implant of FIG. 6;

FIG. 9 is a back view of the patella implant showing a pair of fixation members;

FIG. 10 is a back view of the patella implant showing four fixation members;

FIG. 11 is a cross sectional view of another embodiment of a patella implant according to the present invention;

FIG. 12 is a cross sectional view of one embodiment of a reamer which may be used to prepare a natural patella for acceptance of a patella implant according to the present invention;

FIG. 13 is a side view, partially in cross section, of a second embodiment of a reamer according to the present invention.

DESCRIPTION OF THE PREFERRED EMBODIMENTS

The present invention is of a surgical method and tool for repairing a natural patella of the knee joint. Specifically, the present invention is of a surgical method and tool for reshaping a natural patella and fixing a patella implant to the remaining portion of a natural patella.

The principles and operation of a surgical method and tool according to the present invention may be better understood with reference to the drawings and the accompanying description.

Figure 1:
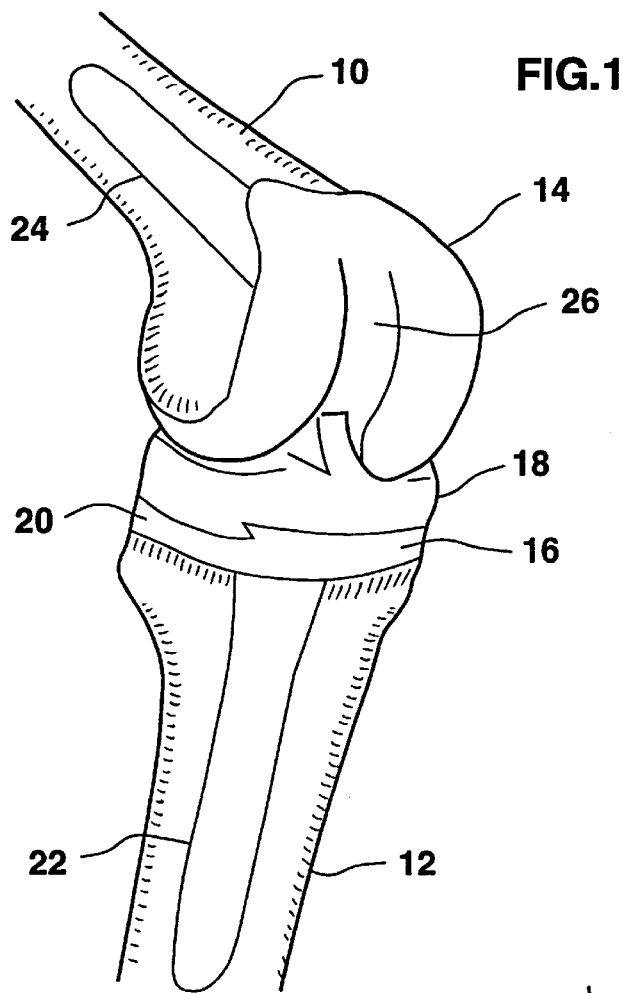
FIG. 1 is perspective view of a typically artificial knee joint.

Referring now to the drawings, FIG. 1 illustrates a typical knee joint prosthesis. The knee joint is formed between the lower end of the femur 10 and the upper end of the tibia 12. In a total knee replacement, the lower end of femur 10 is replaced with a femoral prosthetic component 14 while the upper end of tibia 12 is replaced with a tibial prosthetic component 16.

Tibial prosthetic component 16 is typically made up of a plastic upper plate 18 and a metal back 20. A tibial anchorage stem 22 connected to metal plate 18 is typically used to anchor tibial prosthetic component 16 into tibia 12. Tibial anchorage stem 22 may feature various lengths.

Femoral prosthetic component 14 is typically made of metal and is anchored into femur 10, preferably with a femoral anchorage stem 24. The face of femoral prosthetic component 14 which contacts tibial prosthetic component 16 is typically shaped to mimic the natural knee to include a groove 26. It is on groove 26, or its equivalent, that the patella slides, as can be best be seen in FIG. 2.

Figure 2:
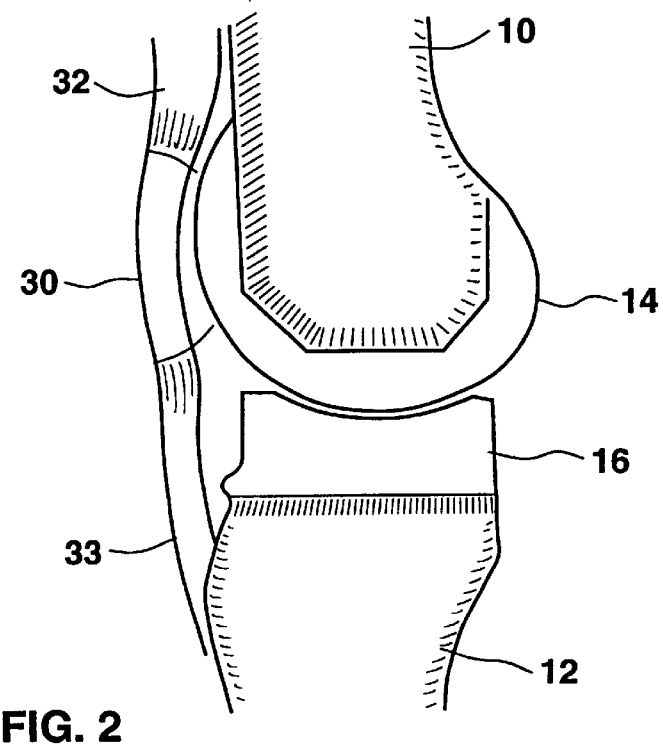
FIG. 2 is a side view of an artificial knee joint as in FIG. 1 showing the patella, quadriceps tendon and patella tendon.

FIG. 2 illustrates a total knee implant including the replacement of the articulating portion (the portion facing the knee) of the patella. As FIG. 2 illustrates, the patella (knee cap) 30 is a disc-shaped member which is connected to the quadriceps tendon 32 and to the patella tendon 33 and is slidable over the lower end of femur 10. The portion of patella 30 facing the knee (the patella implant) is typically, but not necessarily, convex and is dimensioned to slidably engage the corresponding portion of femoral prosthetic component 14, typically groove 26 and the femoral condyles (FIG. 1). The portion of patella 30 away from the knee (the remaining natural patella) is connected to quadriceps tendon 32 and patella tendon 33. Quadriceps tendon 32 is connected to the quadriceps muscle which is, in turn, attached to femur 10. Patella tendon 33 is connected to tibia 12. In this way patella 30 slides over the knee joint during flexion and extension of the joint. The presence of patella 30 facilitates the sliding of quadriceps tendon 32 and further enhances its mechanical efficiency.

To surgically repair a damaged patella what is done is to remove a portion of the articulating surface (the surface facing the knee joint) of the natural patella, leaving the connection between the natural patella and the muscle intact.

Once a portion of the patella has been removed, a prosthetic, or implant, may be fixed to the remaining portion of the natural patella by some suitable means. The implant is shaped to slidably fit within the groove, or its equivalent, of the corresponding natural or prosthetic lower end of the femur, depending on whether the natural lower femur is to remain or be replaced, respectively. Attachment of the implant to the natural patella may be effected with adhesives, cements or other bonding materials and/or through use of pegs, as described in more detail below.

U.S. patent application Ser. No. 08/375,085 discloses a prosthetic patella implant adapted to structurally fit a remaining portion of the natural patella with maximal preserving of healthy natural tissue and minimal wear of the implant.

As shown in FIGS. 3 and 6, the patella implant, 230 or 330, features a substantially convex upper surface, 148 or 248, for sliding over a femoral articulating member; a substantially concave undersurface, 150 or 250, for fixation to a convexly sectioned natural patella; and a circumferential facet, 152 or 252.

When using a polyethylene patella implant, the distance between the upper surface and the undersurface is at least 8 mm or 6 mm for small patients, so as to confer maximal mechanical integrity to the patella implant.

Undersurface, 150 or 250, preferably features a substantially concave shape so as to allow maximal preserving of remaining natural bone tissue. However, undersurface, 150 or 250, may feature a flattened central portion or any other shape which enhances the bonding of the implant to the natural patella.

Figure 15:
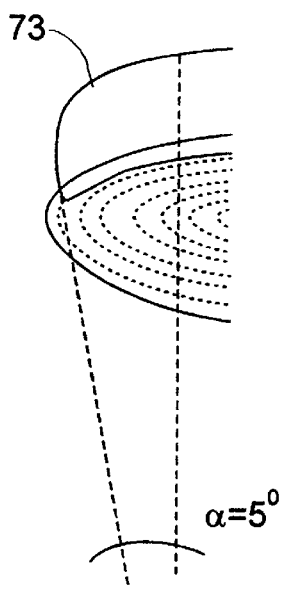
FIGS. 15 and 16 illustrate another embodiment of a method according to the present invention.
Figure 16:
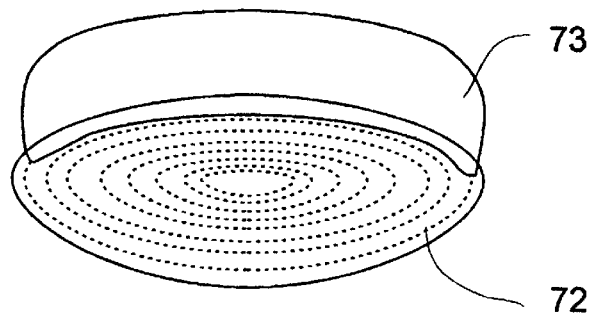

Circumferential facet, 152 or 252, is specifically designed so as to minimize potential damage to necessary blood vessels at the periphery of the natural patella. As shown in FIGS. 3 and 6, circumferential facet, 152 or 252, may feature a cylindrical shape. However, as shown in FIG. 11, circumferential facet 352 may feature a conical shape. A conical circumferential facet may be used for facilitating the attachment of the patella implant to the remaining portion of the natural patella by means of press fitting or other fixation techniques (FIGS. 15 and 16).

As shown in FIGS. 3–11, the patella implant may include one or more pegs 40. Pegs 40 may be of any suitable size. Thus, pegs 40 may extend beyond the lower edge of the circumferential facet (FIGS. 3 and 6). Alternatively, pegs 40 may not extend beyond the lower edge of the circumferential facet (FIG. 11).

Preferably, pegs 40 are formed with circumferential depressions 41 (FIGS. 3 and 6) which improve the bonding and anchorage of the patella implant to the natural bone tissue by providing enhanced friction and further providing space in which cement and the like can accumulate.

The present invention provides a surgical method for repairing a natural patella by reshaping the natural patella and fixing a patella implant to the remaining portion of the natural patella, such that the overall combination of patella implant and remaining natural tissue has maximal biomechanical stability.

Further, the present invention provides a surgical tool for preparing a remaining natural patella to accept the patella implant.

A method according to the present invention includes the step of preparing a natural patella to accept a patella implant having a substantially concave undersurface, such that there is maximal preservation of natural bone tissue and minimal damage to necessary blood vessels at the periphery of the natural patella.

Thus, the natural patella is surgically prepared to preferably adopt a substantially convex shape complementary to the undersurface of the patella implant.

A method according to the present invention may further include the step of drilling at least one hole within the remaining portion of the natural patella for accepting at least one peg, the at least one peg being connected to the patella implant as shown in FIGS. 3–11.

The surgical preparation of the natural patella is preferably carried out using a special surgical tool which cuts the bony patella to precisely the desired shape with minimal interference of its blood supply from the surrounding tissues.

The special tool is a concave surgical reamer 60 (FIG. 12) which can be powered electrically, pneumatically, mechanically, manually, and the like. Reamer 60 can be used to remove an appropriate amount of bone in order to create a convex surface of cortical and/or cancellous bone of the bony patella which accurately fits the concave undersurface of a patella implant according to the present invention.

Reamer 60 includes a concave rotatable reaming member 62 whose concavity is substantially equal to the concavity of the patella implant undersurface. Preferably, reamer 60 further includes a bit 64 which protrudes from concave rotatable reaming member 62 and which is used to simultaneously drill a hole in the natural patella which will accommodate a single central peg extending from the undersurface of the implant.

Bit 64 is also used as a guide means for guiding rotatable reaming member 62 to a predetermined portion of the natural patella so that as reamer 60 is moved the natural patella is shaped to match the undersurface of the patella implant.

Alternatively, bit 64 may feature a blunt end and may be used for guiding reaming member 62 through a substantially central hole pre-drilled in the natural patella.

As shown in FIG. 12, reamer 60 may feature a shaft member 68. Shaft member 68 may feature a circumferential depression 66 having two edges, 66a and 66b, for accepting an external rod (not shown) therein, the rod being connected to an external guiding device. Thus, as reamer 60 is moved, the external rod is moved along depression 66 until it is blocked by edge 66b. The extent of movement of reamer 60 is thus limited by the dimensions of the external rod and depression 66.

Alternatively, as shown in FIG. 13, reamer 60 may include two circumferential extensions, 76a and 76b, the extensions being connected to shaft member 68. Thus, as reamer 60 is moved, the external rod is moved between extensions 76a and 76b until it is blocked by extension 76b. The extent of movement of reamer 60 is thus limited by the dimensions of the external rod and the distance between extensions 76a and 76b.

Circumferential extensions 76a and 76b may be movable along shaft member 68, such that the specific location of extensions 76a and 76b and the distance between the extensions may be adapted to a specific patient.

Rotatable reaming member 62 may feature a flattened central portion or any other shape substantially complementary to the undersurface of the patella implant. Further, reaming member 62 may feature any shape which provides enhanced bonding between the natural patella and the undersurface of the patella implant.

Figure 14:
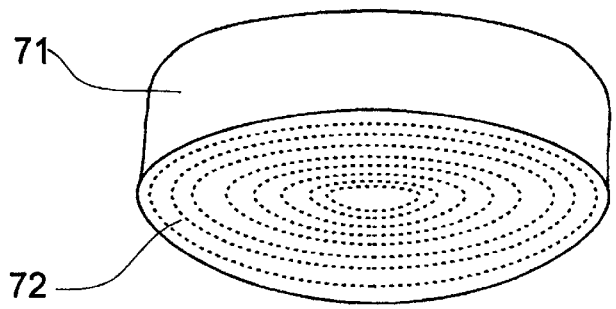
FIG. 14 illustrates one embodiment of a method according to the present invention.

Rotatable reaming member 62 may feature any suitable diameter. The diameter of reaming member 62 may approximately correspond to the diameter of the natural patella. Thus, as shown in FIG. 14, the natural patella 71 may be shaped using reamer 60 so as to accept a patella implant of a substantially equal diameter.

Alternatively, the diameter of reaming member 62 may be smaller than the diameter of the natural patella. Thus, as shown in FIGS. 15 and 16, the natural patella 72 may be shaped using reamer 60 so as to accept a patella implant 73 of a substantially smaller diameter. Such configuration makes it possible to partly intrude patella implant 73 into the natural patella.

Preferably, the patella implant features a cylindrical circumferential facet (FIGS. 3, 6 and 13) or a conical circumferential facet (FIGS. 11, 15 and 16). When using a conical circumferential facet, the angle of the cone is preferably about 5° (FIG. 15). A conical circumferential facet may be used for facilitating the attachment of the patella implant to the remaining portion of the natural patella by means of press fitting or other fixation techniques.

Preferably, fixation of the prosthetic patella implant to the natural patella is further effected by means of a bonding material or other chemical, physical or biological adhesives and by biological reactions, such as bone in growth into the surface, preferably using the pegs which fit into their respective holes in the prepared bone surface.

When using a patella implant with a plurality of pegs 40, their respective holes may be drilled independently by using a conventional drill, following the step of reshaping the natural patella by reamer 60.

While the invention has been described with respect to a limited number of embodiments, it will be appreciated that many variations, modifications and other applications of the invention may be made.

What is claimed is:

1. A method of repairing a natural patella, comprising the steps of:

(a) preparing a natural patella by removing a portion thereof so as to leave a substantially convex remaining portion; and (b) fixing a patella implant onto said substantially convex remaining portion of the natural patella, said patella implant including:
  (i) an upper surface for sliding over a femoral articulating member;
  (ii) a substantially concave undersurface for fixation to said substantially convex remaining portion of the natural patella; and
  (iii) a circumferential facet.

2. The method of claim 1, wherein said patella implant includes at least one peg connected to said undersurface.

3. The method of claim 2, further comprising the step of drilling at least one hole within said remaining portion of the natural patella for accepting said at least one peg.

4. The method of claim 3, wherein said drilling of said hole is carried out simultaneously with said preparation of said natural patella by means of a reamer, said reamer including:
  (i) a substantially concave rotatable reaming member, the concavity of said reaming member being substantially equal to the concavity of said undersurface of said patella implant; and
  (ii) a bit protruding from said concave reaming member for drilling a hole in the natural patella, the bit guiding said rotatable reaming member to a predetermined portion of the natural patella.

5. The method of claim 1, wherein the diameter of said patella implant is substantially equal to the diameter of the natural patella.

6. The method of claim 1, wherein the diameter of said patella implant is smaller than the diameter of the natural patella.

7. The method of claim 1, wherein said circumferential facet is cylindrical.

8. The method of claim 1, wherein said circumferential facet is conical.

9. The method of claim 1, wherein said patella implant partially intrudes into said remaining portion of the natural patella.

10. The method of claim 1, wherein said preparation of said natural patella is carried out using a reamer, the reamer including a substantially concave rotatable reaming member, the concavity of said reaming member being substantially equal to the concavity of said undersurface of said patella implant.

11. The method of claim 10, wherein said preparation of said natural patella is preceded by drilling a hole within said natural patella, and wherein said reaming member includes a bit having a blunt end for guiding said reaming member through said hole.

* * * * *

UNITED STATES PATENT AND TRADEMARK OFFICE
CERTIFICATE OF CORRECTION

PATENT NO.: 5,824,099
DATED: Oct. 20, 1998
INVENTOR(S): Mendes et al.

It is certified that error appear in the above-identified patent and that said Letters Patent is hereby corrected as shown below:

-Drawing 1 in page 1, the number "71" is to be corrected to the number "73"
-Column 6 at line 30, the number "71" is to be corrected to the number "72"

Signed and Sealed this

Fourth Day of May, 1999

Attest:

Q. TODD DICKINSON

*Attesting Officer*       Acting Commissioner of Patents and Trademarks